United States Patent
Sanchez

(10) Patent No.: US 7,832,225 B2
(45) Date of Patent: Nov. 16, 2010

(54) BODY SURFACE COOLING DEVICE AND METHOD FOR APPLICATION OF COSMETICS

(75) Inventor: Marcel Sanchez, Aulnay Sous Bois (FR)

(73) Assignee: L'Oreal, Paris (FR)

(*) Notice: Subject to any disclaimer, the term of this patent is extended or adjusted under 35 U.S.C. 154(b) by 241 days.

(21) Appl. No.: 11/951,917

(22) Filed: Dec. 6, 2007

(65) Prior Publication Data

US 2008/0142036 A1    Jun. 19, 2008

Related U.S. Application Data

(60) Provisional application No. 60/870,663, filed on Dec. 19, 2006.

(30) Foreign Application Priority Data

Dec. 7, 2006    (FR) .................................. 06 55362

(51) Int. Cl.
 *F25D 3/00*    (2006.01)
 *A45D 40/26*   (2006.01)
 *B67D 7/80*    (2010.01)
(52) U.S. Cl. ................. 62/293; 132/320; 222/146.6
(58) Field of Classification Search ............ 62/293; 132/320; 222/146.6
 See application file for complete search history.

(56) References Cited

U.S. PATENT DOCUMENTS 1,833,105 A * 11/1931 Aronson .................... 601/15
2,536,001 A * 12/1950 Chase ....................... 600/555
2,746,264 A    5/1956 Keyes
2,959,038 A * 11/1960 Baird ........................ 62/530
3,259,131 A    7/1966 Kanbar et al.
4,345,598 A    8/1982 Zobac et al.
4,745,909 A * 5/1988 Pelton et al. ................ 601/15
5,331,817 A    7/1994 Anthony
5,738,682 A    4/1998 Jensma
2006/0127733 A1* 6/2006 Kaschmitter et al. ......... 429/34
2007/0044488 A1  3/2007 Habatjou

FOREIGN PATENT DOCUMENTS

EP    0 608 954    8/1994

* cited by examiner

*Primary Examiner*—Frantz F. Jules
*Assistant Examiner*—Cassey Bauer
(74) *Attorney, Agent, or Firm*—Oblon, Spivak, McClelland, Maier & Neustadt, L.L.P.

(57) ABSTRACT

A cooling device includes a cooling arrangement having a refrigerant dispenser. In an illustrated example, the dispenser includes an aerosol container containing the refrigerant and a dispensing valve fitted to a fixing cup which crimps onto the aerosol container. The aerosol container is at least partly housed inside an outer jacket, and a dispensing channel is engaged on the dispensing valve. A cover is mounted on top of the dispensing channel. The cover has an inside face that is impermeable to the refrigerant and at least part of the cover, preferably an outside face of the cover, is made of a material having a thermal conductivity greater than or equal to 1 $Wm^{-1}K^{-1}$. A method of applying a cosmetic product to a body surface is also provided.

39 Claims, 3 Drawing Sheets

BODY SURFACE COOLING DEVICE AND METHOD FOR APPLICATION OF COSMETICS

CROSS-REFERENCE TO RELATED APPLICATIONS

This document claims priority to French Application Number 06 55362, filed Dec. 7, 2006 and U.S. Provisional Application No. 60/870,663, filed Dec. 19, 2006, the entire contents of which are hereby incorporated by reference.

FIELD OF THE INVENTION

The present invention relates to a cooling device. An important but not exclusive application of the present invention is for cooling a body surface with the aim of locally improving the penetration of a cosmetic product. "Cosmetic product" as used here means a product as defined in European Council Directive 93/35/EEC of 14 Jun. 1993.

BACKGROUND OF THE INVENTION

Discussion of Background

In some cases it is advantageous to chill part of the surface of the body in order to give the user a sensation of freshness and well-being. Similarly it is sometimes desirable to apply a cosmetic product at a low temperature in order to enhance its effect.

In order to cool a cosmetic product, the user can keep the product in a refrigerator before applying it. However, a problem with this method is that in very hot weather the cosmetic product quickly warms up as soon as it is taken out of the refrigerator. As a result, the user no longer benefits from the sought-after refreshing effect.

Devices for cooling a body surface have therefore been developed in the prior art.

EP 0 608 954 discloses an example of a prior-art device capable of cooling a cutaneous surface. That device comprises a pressurized container containing a refrigerant. The container is provided with a dispensing valve for dispensing the refrigerant when desired. The valve has an orifice capable of communicating with a dispensing channel. The dispensing channel supplies a porous applicator designed for applying the liquid refrigerant to a target surface.

However, a problem with such a device is that the surface area of the applicator in contact with the skin is very small, meaning that the treatment is highly localized. In addition, the refrigerant can be dispensed at between −20° C. and 0° C. and cannot therefore be kept in contact with the skin for a long period without risking burning of the skin. Prolonged cooling with such a device is therefore undesirable or out of the question.

SUMMARY OF THE INVENTION

It is therefore an object of the present invention to overcome the above mentioned problems.

It is also an object of the present invention to provide a cooling device suitable for maintaining a cooling action for a long period of time on a target body surface.

It is a further object of the present invention to provide a rechargeable device that is easy to hold in the hand.

Another object of the present invention is to provide a device that is easy to manufacture and to use and that has a relatively low cost or manufacturing price.

For this purpose, according to an example of the present invention, a cooling device is provided which includes a cooling means or cooling assembly having a refrigerant container and dispenser. In accordance with an example, the assembly can include an aerosol container containing the refrigerant and a dispenser such as a dispensing valve of the type fitted to a fixing cup which crimps onto the aerosol container. The aerosol container is at least partly housed inside an outer jacket, and a dispensing channel is engaged on the dispensing valve. A cover is mounted on top of the dispensing channel, and the cover has an inside face that is impermeable to the refrigerant. In addition at least part of the cover, notably an outside face of the cover, is made of a material having a thermal conductivity greater than or equal to 1 $Wm^{-1}K^{-1}$ (watt per meter kelvin).

By way of example, this cover may be made in one piece with the outer jacket, or in an advantageous embodiment it may be mounted on the outer jacket. The cover can be engaged on and fixed to the outer jacket, or can be movably coupled to the outer jacket.

The thermal conductivity may be between 10 and 430 $Wm^{-1}K^{-1}$ and more preferably between 20 and 240 $Wm^{-1}K^{-1}$.

The material having a thermal conductivity greater than or equal to 1 $Wm^{-1}K^{-1}$ may be a metallic material and in particular, for example, titanium, steel, platinum or aluminium.

According to an example, the container can have a first end provided with the dispensing valve and a second or closed end, with the first and second ends joined by a side wall, and the outer jacket at least partly enveloping the side wall.

Also by way of example, the cover may be detachable. In the assembled position of the cover, the cover can be designed or arranged to abut against the outer jacket. In the assembled position of the cover, the inside and outside faces can be oriented in an invariable manner (or fixed position) relative to the dispensing channel. Further by way of example, the device can include a means or arrangement for immobilizing the cover on the dispensing channel and/or on the outer jacket. The cover can be fixed to the dispensing channel by press-fitting, by screwing or by snap-fastening.

By way of example, the outer jacket and the dispensing channel can be made in one piece.

Also by way of example, the device can include a means or arrangement for adjusting the volume under the cover or the volume defined between the dispensing channel and the cover.

The outside face of the cover can have a convex surface, for example.

The present invention also relates to a method of applying a cosmetic product to a body surface. A preferred example includes a first step of applying the cosmetic product to the body surface, followed by a second step of massaging the cosmetic product-covered body surface using a device according to the invention.

As should be apparent, the invention can provide a number of advantageous features and benefits. It is to be understood that, in practicing the invention, an embodiment can be constructed to include one or more features or benefits of embodiments disclosed herein, but not others. Accordingly, it is to be understood that the preferred embodiments discussed herein are provided as examples and are not to be construed as limiting, particularly since embodiments can be formed to practice the invention that do not include each of the features of the disclosed examples.

BRIEF DESCRIPTION OF THE DRAWINGS

A better understanding of the invention will be gained from reading the following description in conjunction with the accompanying figures. The figures are offered purely as a guide and by way of example, and in no way limit the invention.

DETAILED DESCRIPTION OF THE PREFERRED EMBODIMENTS

Figure 1:
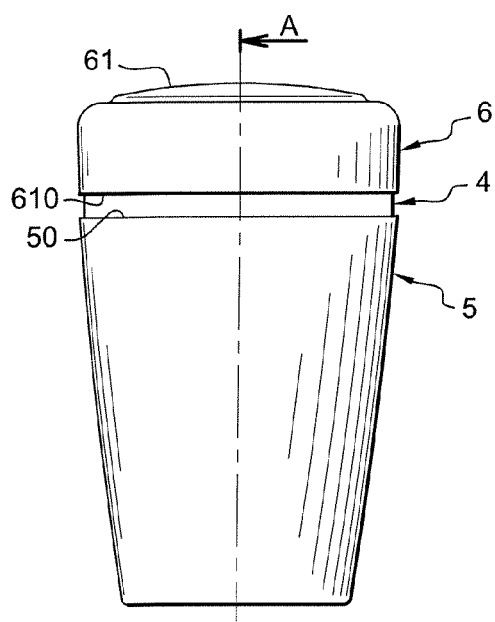
FIG. 1 is a diagrammatic perspective view of an embodiment of a device according to the invention.

Referring now to the drawings, like reference numerals are utilized to designate identical or corresponding parts throughout the several views.

Figure 2:
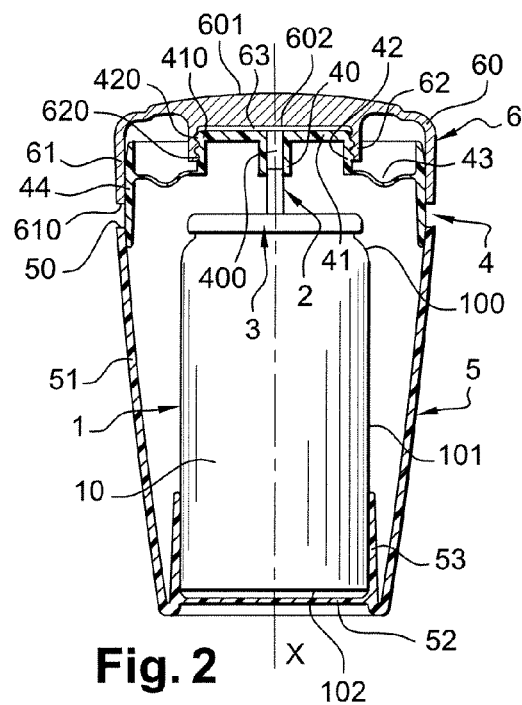
FIG. 2 is a diagrammatic view in longitudinal section on the cutting plane A-A through the device shown in FIG. 1.

With reference to an example as shown FIGS. 1 and 2, the device according to an example of the invention includes a cooling means or a cooling assembly 1.

In the illustrated example, the cooling means 1 includes a refrigerant dispenser comprising an aerosol container 10 containing the refrigerant. The refrigerant may for example be a gas which is in a liquefied state while it is under pressure in the container and whose temperature falls in a vaporized state when it expands. This refrigerant may for example be a hydrocarbon such as 2,3-butane, dimethyl ether or propane, or it may be a freon such as HFC-134a.

The aerosol container includes a first or open end 100 and a second or closed end 102, with the first and second ends being joined by a side wall 101. This container can be in the general form of a cylinder of revolution, for example.

In the illustrated example, the first end 100 is equipped with a dispensing valve 2. This dispensing valve 2 is designed to selectively dispense the refrigerant contained inside the aerosol container. The dispensing valve 2 may be connected to the aerosol container in a conventional way by a fixing cup 3 which crimps onto the first or open end 100 of the aerosol container. This dispensing valve may be crimped onto the outside or inside of the first or open end of the container. Internal crimping is also known as expansion.

By way of example, the dispensing valve 2 can be operated by pushing it down and/or tilting it, causing the refrigerant to be released in a defined quantity or continuously. Such a valve generally can include a valve stem operated by movement relative to the container. This valve stem can be moved relative to a valve body. The valve body may optionally define a chamber defining the quantity of refrigerant to be dispensed, for example. A valve body of this kind can be mounted on the first or open end of the container by means of the fixing cup which is crimped on. A push-down valve includes, for example, a valve stem capable of back-and-forth movement relative to the valve body and more generally relative to the container. This valve, and in particular the valve stem, generally defines an internal channel through which the refrigerant is expelled and which sets up selective communication with the valve body and more generally with the contents of the container. Thus, when the valve stem is moved by a user, the expulsion channel can communicate with the inside of the aerosol container and said refrigerant can thus be dispensed.

In the present illustrative embodiment, the dispensing valve 2 includes a push-down valve stem. This valve stem can be moved axially relative to the pressurized container 1 between a rest position and a dispensing position. For this purpose, the valve stem is usually press-fitted into an actuating member 4. Once inside, the valve stem is locked to the movements of the actuating member 4 in this example. Valve actuation is now triggered by a relative movement between the actuating member 4 and the aerosol container 10.

In the illustrated example, the aerosol container is housed in an outer jacket 5. This outer jacket envelopes at least part of the side wall 101 of the container.

As shown in the example of FIGS. 1 and 2, the outer jacket 5 can have a rim 50 defining an opening, which may be circular, and a base 52. This rim and this base are joined by a cylindrical wall 51. The jacket is roughly bucket-shaped in the illustrated example.

The container 1 can be inserted through the opening of the outer jacket. In this example the jacket is as tall as the container. The rim 50 of the jacket is level with the first or open end 100, such that the jacket completely surrounds the pressurized container.

The outer jacket defines the surface which the user grips. This jacket is preferably at least partly made from a material having a thermal conductivity of less than $1\ Wm^{-1}K^{-1}$. This jacket may for example comprise a plastic such as polyethylene, polyamide or polyoxymethylene or a cellular material such as a foam. The jacket is preferably opaque so that the container is completely masked. However, a slot could, if desired, be made in the jacket so that the container would be partly visible from the outside. Such a jacket can therefore have both an aesthetic function and make it easier to grip the device in the hand.

The outer jacket 5 can also have retention means or arrangement 53 rising from the base of the jacket 52. The retention arrangement can include, for example, a ring in which a part of the aerosol container can be inserted, preferably making a tight fit. The part housed in this ring can, for example, extend from the second or closed end 102 to a quarter of the way up the container body. Such retention means will then limit lateral and preferably axial movement of the pressurized container relative to the outer jacket 5.

By way of example, the actuating member 4 includes a dispensing channel 40, a platform 41, a peripheral skirt 42, a resilient element or resilient means 43, and a mounting collar 44.

The dispensing channel 40 is, for example, press-fitted onto the valve stem to channel the product dispensed by the valve 2. The channel passes through the platform 41 and opens out at a hole 400. This channel lies on a longitudinal axis X, which in this example coincides with an axis of revolution of the container. The platform 41 extends radially away from the hole 400. The platform 41 has a circular outer edge 410 in the illustrated example.

The peripheral skirt 42 then descends from the outer edge 410. The illustrated example of a peripheral skirt includes an outer surface provided with fixing means or a fixing arrangement 420 designed to engage with a cover 6 as will be explained later in this description. These fixing means advantageously include threads 420, for example.

The resilient means or resilient element 43 connects the peripheral skirt 42 to the mounting collar 44. The resilient means 43 can include a plurality of flexible tabs, for example six tabs, extending for example at regular intervals between the peripheral skirt 42 and the mounting collar 44. Alternatively, by way of example, the resilient means or resilient element can include an elastic annulus fitted between the peripheral skirt 42 and the mounting collar 44.

In the example shown, the mounting collar 44 is engaged tightly in the opening of the outer jacket 5. This mounting collar is thus mounted securely in the outer jacket. However, the resilient element 43 allows the channel 40, platform 41 and peripheral skirt 42 to be moved axially relative to the mounting collar 44 in order to permit operation of the dispensing valve 2.

The cover 6 can include a covering part 60 and a side skirt 61, for example. The covering part 60 is placed over the hole 400 of the actuating member 4 so as to be in direct contact with the dispensed product. This covering part has an outside face 601 and an inside face 602.

According to a preferred example, the inside face 602 is impermeable to the refrigerant. In other words, this inside face ensures that refrigerant exiting the dispensing channel 40 is prevented from passing through the cover and coming into direct contact with the skin. Additionally, the cover is made at least partly of a material having a thermal conductivity greater than or equal to 1 $Wm^{-1}K^{-1}$, preferably between 10 and 430 $Wm^{-1}K^{-1}$, and more preferably between 20 and 240 $Wm^{-1}K^{-1}$.

According to an example, the cover may therefore be made entirely of such a material. Alternatively, only part of the cover, for example the covering part 60, may be made of such a material. For example, this material may extend from the inside face to the outside face of the covering part so that heat is easily conducted through this covering part. This conductivity therefore allows the refrigerant to cool the outside face of the covering part 60 and ensures a good distribution of heat extraction across the covering part.

Alternatively, by way of example, the inside face may be made of a material having a thermal conductivity of less than 1 $Wm^{-1}K^{-1}$ and the outside face may be made of a material that has a thermal conductivity greater than 1 $Wm^{-1}K^{-1}$, or vice versa.

The material having a thermal conductivity greater than 1 $Wm^{-1}K^{-1}$ may also be in the form of at least one insert housed in the covering part. This insert preferably extends transversely relative to the longitudinal axis X of the dispensing channel 40. This insert may be embedded in a material that has a thermal conductivity of less than 1 $Wm^{-1}K^{-1}$. Such an insert may therefore be situated at a distance from the outside face and from the inside face of the covering part. The outer and inside faces of the covering part may therefore have a thermal conductivity of less than 1 $Wm^{-1}K^{-1}$.

The material having a thermal conductivity greater than or equal to 1 $Wm^{-1}K^{-1}$ may for example be titanium, which has a thermal conductivity of approximately 20 $Wm^{-1}K^{-1}$, stainless steel comprising for example 18% chrome and 8% nickel, which has a thermal conductivity of approximately 26 $Wm^{-1}K^{-1}$, mild steel, which has a thermal conductivity of approximately 46 $Wm^{-1}K^{-1}$, platinum, which has a thermal conductivity of approximately 72 $Wm^{-1}K^{-1}$, an Al—SiC alloy, which has a thermal conductivity of between 150 and 200 $Wm^{-1}K^{-1}$, aluminium, which has a thermal conductivity of approximately 240 $Wm^{-1}K^{-1}$, copper, which has a thermal conductivity of approximately 400 $Wm^{-1}K^{-1}$, or silver, which has a thermal conductivity of approximately 430 $Wm^{-1}K^{-1}$.

In the illustrated example, the outside face 601 of the covering part preferably forms a massaging element. This massaging element can occupy all of the surface of the covering part or merely a part. The outside face 601 preferably has at least one relief. This relief may for example include a convex surface. Such a convex surface will restrict the area of contact with the surface of the body which is being massaged and thus enhance the massaging action. The design of the device is ergonomically suitable for massaging the desired surface of the body.

Figure 9:
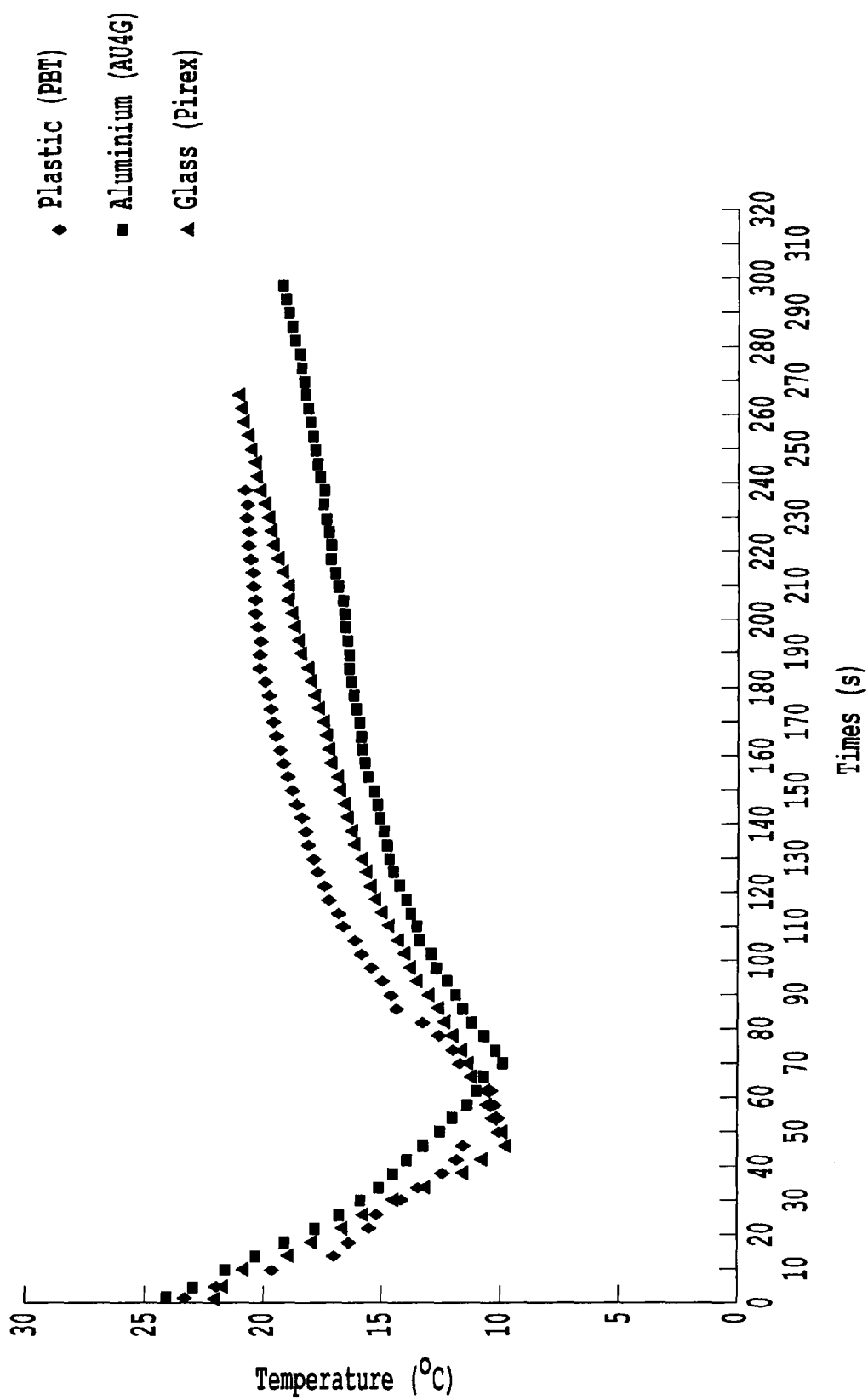
FIG. 9 is a graph showing how various materials warm up as a function of time.

FIG. 9 is a graph showing the temperature of the outside face of the covering part as a function of time. In the present example, a metering valve delivering 150 μl of refrigerant—in this example 2,3-butane—with each actuation is used to cool the inside face of the covering part under test.

This test is performed on a covering part made either of polybutylene terephthalate (PBT), which has a thermal conductivity of 0.21 $Wm^{-1}K^{-1}$, or Pyrex, which has a thermal conductivity of 1.16 $Wm^{-1}K^{-1}$, or aluminium AU4G 2017A, which has a thermal conductivity of 134 $Wm^{-1}K^{-1}$. The materials used are each in the form of a 1-mm thick layer.

In this test or example, the inside face of the various covering parts is first cooled. This is done by releasing refrigerant directly onto the inside face of the covering parts. Cooling is applied until the temperature of the outside face of the covering parts is 10° C. Once this temperature has been reached, the various covering parts are left at room temperature and the warming up of their outside faces is observed.

The graph shows more rapid warming up of the covering parts made of PBT than of the covering parts made of Pyrex and aluminium. The use of materials having a thermal conductivity greater than or equal to 1 $Wm^{-1}K^{-1}$ thus maintains a cooling action of the outside face of the covering part for a longer time. These materials thus provide a longer-lasting cooling action for an equal or smaller quantity of refrigerant dispensed.

The cover 6 can include a fixing means or a fixing arrangement for attaching the cover to the actuating member 4. This cover 6 is preferably detachable to allow cleaning of the actuating member and of the inside face of the covering part. However, the cover and outer jacket could also be made in one piece (not shown), for example, with the cover and the outer jacket made of a material having a thermal conductivity greater than or equal to 1 $Wm^{-1}K^{-1}$.

The fixing arrangement could be provided on an annulus 62 extending away from the inside face 602 of the covering part. This annulus can include, for example, an inside surface with threads 620 for mating with the threads 420 of the peripheral skirt of the actuating member. In this case, the cover is fixed to the actuating member by screwing it on. It would also be possible to fix the cover to the actuating member by press-fitting or by snap-fastening, for example. In the second case, an annular bead may for example be formed on the inside surface of the annulus 62 to engage with a corresponding groove in the outside surface of the peripheral skirt 42, or vice versa.

With such fixing means or arrangement 420, 620, the cover 6 can be immobilized relative to the dispensing channel. In use, therefore, the cover is able to remain stationary with respect to the rest of the device when it is moved over the surface of the body to be treated.

The inside face 602 of the covering part and the dispensing channel 40 may be at a greater or lesser distance from each other. The platform 41 and the covering part 60 may thus define between themselves a refrigerant receiving space 63 of variable volume, for example. The fixing arrangement can be used for making such an adjustment.

For example, as the cover 6 is screwed down or up relative to the actuating member 4, a space 63 of smaller or greater volume is defined between the covering part 60 and the platform 41. If snap-fastening is employed, a plurality of annular beads may be formed on the inside surface of the annulus 62: such beads will then form nicks which drop into one or more corresponding grooves formed in the outside surface of the peripheral skirt 42. If press-fitting is employed, friction between the inside surface of the annulus 62 and the outside surface of the peripheral skirt 42 will also allow adjustment of the volume defined between the covering part 60 and the platform 41.

In the illustrated example, when the cover is in the mounted position, the outside face 601 and the inside face 602 of the covering part 60 are oriented in an invariable or fixed position relative to the dispensing channel 40. The cover cannot therefore be rotated upon itself, so the refrigerant exiting the dispensing channel 40 can only come into contact with the inside face of the covering part.

In this example, the side skirt 61 of the cover extends away from the outer edge of the covering part 60. This side skirt has a free edge 610. The skirt can be located around the actuating member 4 and in particular around the mounting collar. The mounting collar and the side skirt can thus be concentric, for example. The collar may in particular make a non-tight fit around this skirt so that the collar forms a guide wall for the skirt when the cover is moved. The rim 50 of the outer jacket can form a stop for the free edge of the side skirt so as to limit the cover's range of movement.

The operation of an example of a device according to the present invention will now be described with reference to FIGS. 1 and 2.

The user may first apply a cosmetic product, such as an anti-wrinkle product, onto a body surface, such as the face. Next, the user can grasp the device by holding it around the outer jacket 5. To create a cooling action, the user applies pressure to the cover 6, and specifically the covering part 60, in order to actuate the dispensing valve 2. The refrigerant exiting from the aerosol container can then travel first along the expulsion channel of the valve and then along the dispensing channel 40. The refrigerant then enters the space 63 below the cover, in the illustrated example defined by the actuating member 4 and the cover 6. The refrigerant thus comes into contact with the inside face 602 of the covering part. As the refrigerant strikes the inside face 602, it is redirected sideways, ensuring a good distribution of the cooling action across the covering part. The refrigerant can then be evacuated from the space 63 via a venting passage between the peripheral skirt 42 and the annulus 62.

The material from which this cover is made allows good conduction of heat through this covering part so that the outside face of the covering part is chilled immediately. The user can then position the outside face of the covering part against the desired surface of the body. The outside face simultaneously cools the cosmetic product and the body surface to which this cosmetic product has been applied.

The cooling action gives the user a sensation of well-being and can also promote the penetration of the cosmetic product into the skin, where it can act more effectively. The convexity of the outside face can also provide a localized and efficient massaging of the body surface and can thus enhance the diffusion of the cosmetic product through the skin.

FIGS. 3 to 8 show three other embodiments as examples of a device according to the present invention. For the sake of clarity, similar reference numbers are given to similar parts in the different embodiments, and parts that differ between these embodiments have reference numbers followed by a quotation mark or double quote. Only these differences will be discussed in the remainder of the description.

Figure 3:
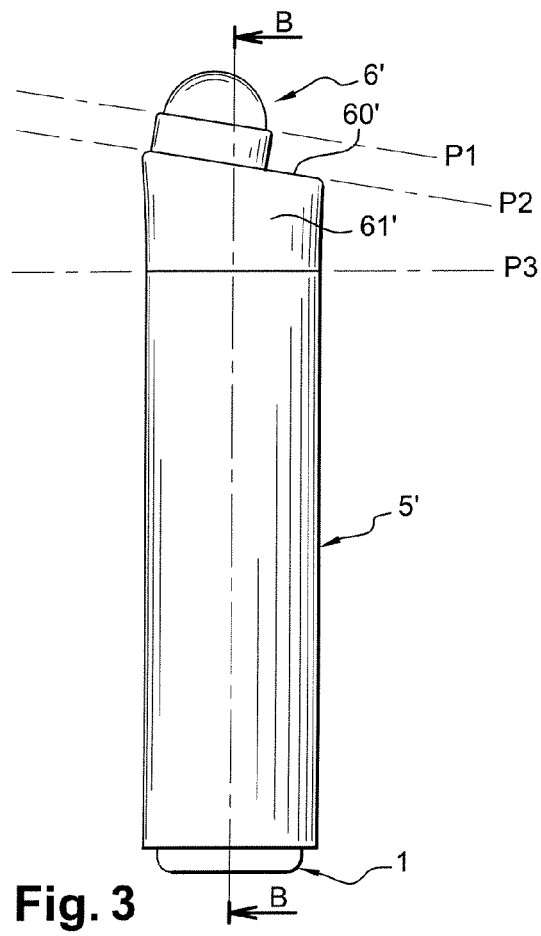
FIG. 3 is a diagrammatic perspective view of another embodiment of a device according to the invention.
Figure 4:
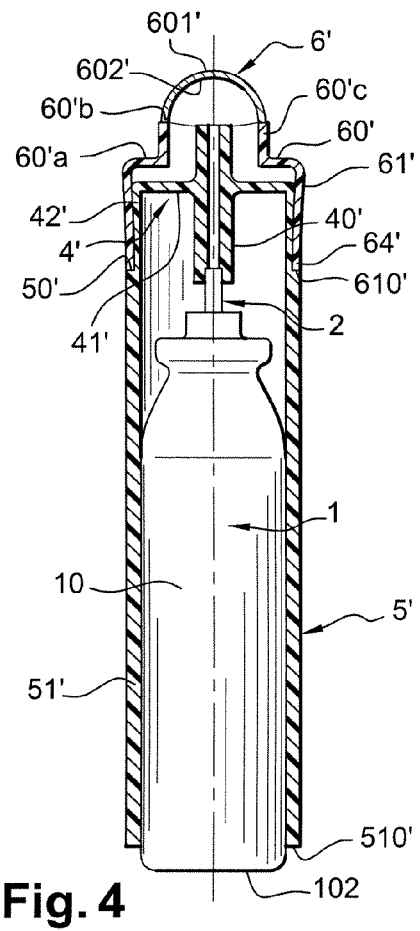
FIG. 4 is a diagrammatic view in longitudinal section on the cutting plane B-B through the device shown in FIG. 3.

FIGS. 3 and 4 show a second embodiment of a device according to an example of the present invention. This device includes an outer jacket 5' with a cylindrical wall 51' that has an unattached open end 510'. This outer jacket thus has no base. At the other end, the outer jacket has an edge 50' in the illustrated example.

In this embodiment the outer jacket 5' and the actuating member 4' are produced in one piece. The actuating member has a dispensing channel 40', and from this there extends radially a platform 41' bordered by a peripheral skirt 42'. The dispensing channel 40' may extend on either side (or both sides) of this platform 41'.

In the illustrated example, the peripheral skirt 42' may be thinner than the cylindrical wall 51' of the outer jacket, so that the edge 50' forms an outward step relative to the peripheral skirt. In this illustrative example, the cover includes a tiered covering part 60'. In particular, the covering part has a shoulder 60'a from which a platform 60'b with a massaging element rises. The platform and the shoulder may be connected by an annular wall 60'c. The platform and the shoulder lie in planes P1 and P2, respectively, which may be parallel, for example. Only the massaging element needs to be made (or partially made) of a material having a thermal conductivity greater than or equal to 1 $Wm^{-1}K^{-1}$. In this embodiment, this massaging element is hemispherical.

In the assembled position, the side skirt 61' of the cover 6' fits around the peripheral skirt 42' of the actuating member 4'. The shoulder 60' is positioned over the platform 41' and the dispensing channel is positioned underneath the massaging element. A space of variable volume can be provided between the covering part and the actuating member, for example between the massaging element and the dispensing channel, as well as between the shoulder and the platform.

The peripheral skirt 42' may have a free edge 610' designed to abut against the outward step 50' of the outer jacket. However, a gap 64' may be provided between this free edge 610' and the outward step 50', in which case the gap may be in fluid communication with the space defined between the covering part and the actuating member. If so, this gap can define a venting orifice.

The free edge 610' may lie in a plane P3 at right angles to the cylinder axis X. This plane P3 may intersect the planes P1 and P2.

In this embodiment, the aerosol container 1 projects from the unattached end 510' of the outer jacket so that in order to actuate the dispensing valve 2, the user has to depress the second or closed end 102 of the aerosol container 1. Depressing it moves the container relative to the valve 2 which is held in the dispensing channel 40' and causes refrigerant to be dispensed onto the inside face of the covering part 602'. The cooling action then spreads from the inside face to the outside face. The user can then massage a body surface which may optionally be covered with a cosmetic product.

Figure 5:
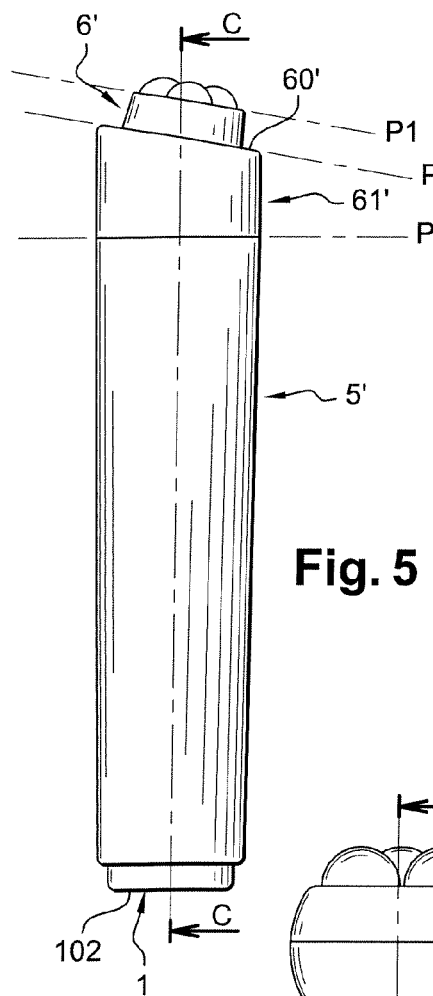
FIG. 5 is a diagrammatic perspective view of another embodiment of a device according to the invention.
Figure 6:
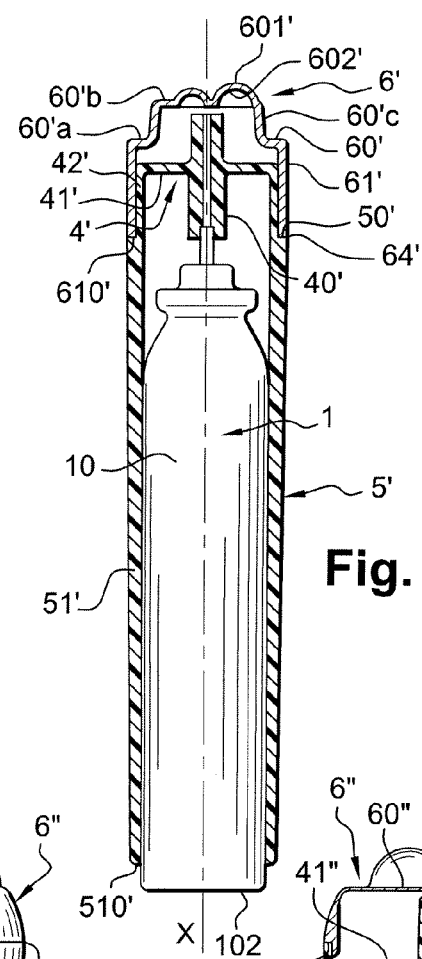
FIG. 6 is a diagrammatic view in longitudinal section of the cutting plane C-C through the device shown in FIG. 5.

FIGS. 5 and 6 show a third example of an embodiment of a device of the present invention. This device differs from the device shown in FIGS. 3 and 4 in that the platform 60' has several massaging elements. The figure shows three such massaging elements.

Figure 7:
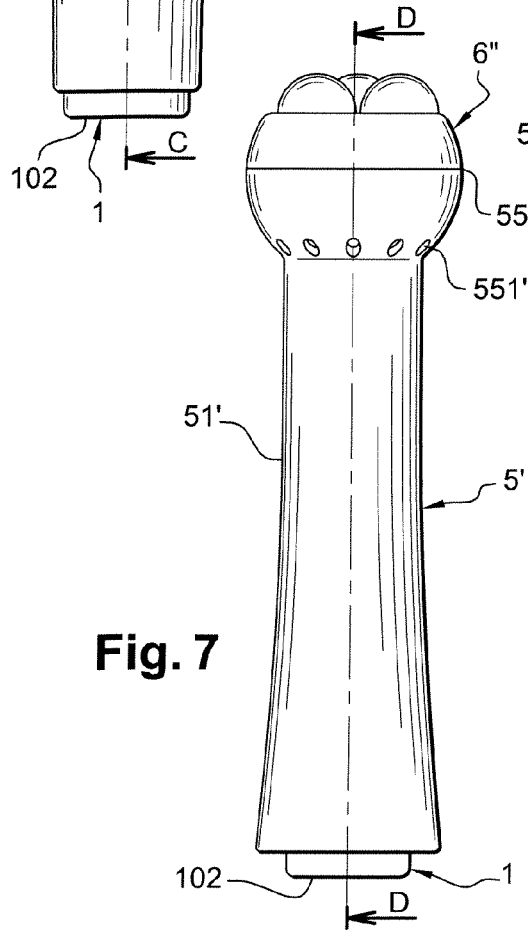
FIG. 7 is a diagrammatic perspective view of another embodiment of a device according to the invention.
Figure 8:
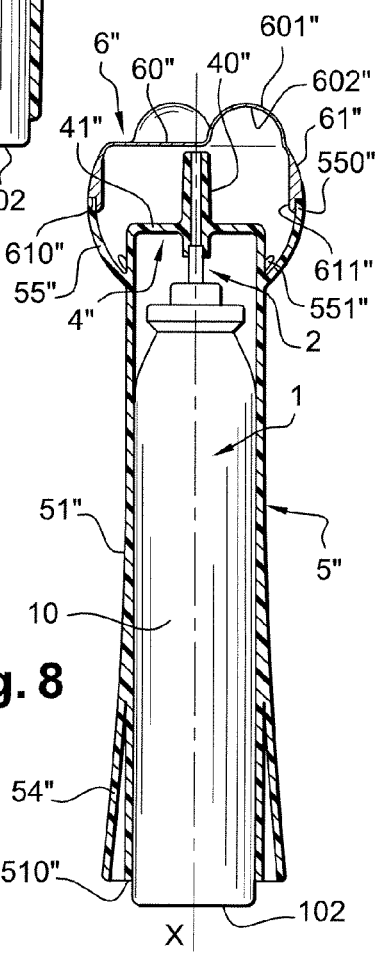
FIG. 8 is a diagrammatic view in longitudinal section on the cutting plane D-D through the device shown in FIG. 7.

FIGS. 7 and 8 show a fourth example of an embodiment of a device of the present invention. This device differs from the device shown in FIGS. 5 and 6 in that the outer jacket 5" includes a cylindrical wall 51" (or circular cross-section) with outward-flaring fins 54". These fins may extend as far as the unattached end 510" of the outer jacket. Such fins make the device easier to hold in the hand. The outer jacket 5" also has a flared part in the form of a bulb 55". This bulb has a free edge 550". This device has a cover 6" which includes a covering part 60" bordered by a side skirt 61" which has a free edge 610". In this example, the covering part 60" includes several massaging elements, such as three massaging elements. The side skirt 61" has an outside face having a rounded profile. In the assembled position, the free edge 610" of the side skirt abuts against the free edge 550" of the bulb. The free edge 610" may have an inside annular lip 611" to form a tight fit against an inside surface of said bulb. This lip thus guides the cover when it is fitted onto the bulb and secures the cover to this bulb. Optionally, one or more vent apertures or holes can be provided as shown at 551', 551". Because the vent holes are at a location spaced from the skin-contacting surface, the refrigerant will not be expelled directly onto the skin or the surface which contacts the skin. As shown in the illustrated example, the vent holes are preferably arranged such that they open in a direction away from the surface of the covering part that will contact the skin.

These different embodiments work in a similar way to the first embodiment and will not therefore be explained any further.

Throughout the description, expressions such as "including a," "comprising a," or "having a" etc. are to be taken as synonymous with "having at least one" unless otherwise specified.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A cooling device comprising:
   cooling means having a refrigerant dispenser comprising an aerosol container containing a refrigerant and a dispensing valve fitted to a fixing cup which crimps onto the aerosol container, said aerosol container being at least partly housed inside an outer jacket;
   a dispensing channel;
   a mounting arrangement which mounts and positions the dispensing channel such that the dispensing channel extends through the mounting arrangement, wherein the dispensing channel includes a first opening on one side of the mounting arrangement and a second opening on a second side of the mounting arrangement, and wherein the mounting arrangement positions the dispensing channel such that the first opening is coupled to the dispensing valve;
   a cover mounted above said dispensing channel and above the mounting arrangement;
   wherein the mounting arrangement and dispensing channel are arranged to move relative to the aerosol container and thereby move the dispensing valve between actuated and non-actuated positions, wherein in the actuated position the refrigerant passes through the dispensing valve and into the dispensing channel and the refrigerant exits the second opening of the dispensing channel and is directed toward the cover, and further wherein the dispensing valve is selectively movable between the actuated and non-actuated positions to selectively open and close the dispensing valve;
   wherein the mounting arrangement includes a platform through which the dispensing channel extends, and wherein said platform forms a barrier separating a first portion of said device from a second portion of said device, and wherein said first portion includes a chamber defined between said platform and said cover, and further wherein the container is positioned in said second portion, and wherein upon actuation of the dispensing valve the refrigerant passes through the dispensing channel and into said chamber, and wherein the platform maintains the chamber separated from the container; and
   wherein said cover includes an inside face that is impermeable to the refrigerant, and wherein at least part of the cover is made of a material having a thermal conductivity greater than or equal to 1 $Wm^{-1}K^{-1}$.

2. The cooling device according to claim 1, wherein at least part of an outside face of said cover is made of said material.

3. The cooling device according to claim 2, wherein said thermal conductivity is between 10 and 430 $Wm^{-1}K^{-1}$.

4. The cooling device according to claim 3, wherein said thermal conductivity is between 20 and 240 $Wm^{-1}K^{-1}$.

5. The cooling device according to claim 1, wherein said material having a thermal conductivity greater than or equal to 1 $Wm^{-1}K^{-1}$ is a metallic material.

6. The cooling device according to claim 5, wherein the metallic material includes at least one material selected from the group consisting of titanium, steel, platinum, and aluminium.

7. The cooling device according to claim 1, wherein said container has a first end provided with said dispensing valve and a second end, wherein said first and second ends are joined by a side wall, and wherein said outer jacket at least partly envelopes said side wall.

8. The cooling device according to claim 1, wherein said cover is detachable.

9. The cooling device according to claim 1, wherein said cover is fixed to said mounting arrangement by one of press-fitting, screwing or snap-fastening.

10. The cooling device according to claim 1, wherein said cover is arranged to abut against said outer jacket.

11. The cooling device according to claim 1, wherein said cover and said outer jacket are formed as one piece.

12. The cooling device according to claim 2, wherein said inside and outside faces of the cover are fixed relative to said dispensing channel.

13. The cooling device according to claim 1, further comprising means for immobilizing said cover with respect to said dispensing channel and/or on said outer jacket.

14. The cooling device according to claim 1, wherein said outer jacket, said mounting arrangement, and said dispensing channel are formed as one piece.

15. The cooling device according to claim 1, further comprising means for adjusting a volume of said chamber defined between said platform and said cover.

16. The cooling device according to claim 2, wherein said outside face has a convex surface.

17. The cooling device according to claim 2, wherein said outside face of said cover includes at least one massage surface.

18. A method of applying a cosmetic product to a body surface, comprising a first step of applying said cosmetic product to said body surface, followed by a second step of massaging said cosmetic product-covered body surface using the cooling device according to claim 1.

19. A cooling device comprising:
a cooling assembly which includes an aerosol container containing refrigerant and a dispenser which dispenses said refrigerant from said container;
a cover, said cover including an inside face that is impermeable to said refrigerant, said cover further including an outside face;
wherein the device includes a platform which is coupled to said dispenser, and wherein a chamber is defined between said platform and said cover, and wherein the platform forms a barrier separating the container from the chamber such that the container is positioned outside of said chamber and the container is maintained separated from the chamber, and further wherein the refrigerant passes from the container and through the platform into the chamber by way of the dispenser, and wherein said cover is arranged such that the refrigerant dispensed by said dispenser cools said inside face and thereby cools said outside face of said cover; and
wherein at least a portion of said cover comprises a material having a thermal conductivity greater than or equal to 1 $Wm^{-1}K^{-1}$.

20. The cooling device according to claim 19, wherein said chamber includes a volume, and wherein a size of said volume is adjustable independently of actuation of the dispenser.

21. The cooling device according to claim 19, further including an outer jacket which at least partially houses said container, and wherein said cover is coupled to said outer jacket.

22. The cooling device according to claim 21, wherein said cover is axially slidable relative to said outer jacket, and wherein movement of the cover relative to the outer jacket causes the refrigerant to be dispensed by the dispenser.

23. The cooling device according to claim 19, wherein said dispenser includes a dispensing valve and a dispensing channel, wherein said dispensing valve is mounted to the container, and wherein said cover is mounted above said dispensing channel, and wherein said dispensing channel extends through said platform, said dispensing channel including a first opening coupled to said dispensing valve and a second opening through which the refrigerant exits the dispensing channel into the chamber.

24. The cooling device according to claim 19, further including an outer jacket partially housing said container, and wherein the container partially protrudes from and is movable relative to said outer jacket, and wherein movement of the container relative to the outer jacket causes the refrigerant to be dispensed by said dispenser.

25. The cooling device according to claim 19, wherein said thermal conductivity is between 10 and 430 $Wm^{-1}K^{-1}$.

26. The cooling device according to claim 19, wherein said thermal conductivity is between 20 and 240 $Wm^{-1}K^{-1}$.

27. The cooling device according to claim 19, wherein at least a portion of the outside face of the cover is formed of said material.

28. The cooling device according to claim 27, wherein said outside face includes at least one massage surface.

29. The cooling device according to claim 1, wherein said platform is part of an actuating member which is mounted for sliding axial movement relative to said container to actuate said dispensing valve.

30. The cooling device according to claim 29, wherein the outer jacket extends over a portion of the container, and wherein a portion of the container protrudes from said outer jacket, and further wherein said platform is coupled to said jacket such that relative axial sliding movement between said outer jacket and said container causes actuation of said dispensing valve.

31. The cooling device according to claim 29, wherein the platform is coupled to the cover, wherein the container is at least partially enclosed by the outer jacket, and wherein the cover is slidably movable relative to the outer jacket in an axial direction such that axial sliding movement of the cover relative to the outer jacket causes actuation of the dispensing valve.

32. The cooling device according to claim 31, wherein a mounting collar is associated with said outer jacket, and wherein the cover axially slides over an outer periphery of the mounting collar.

33. The cooling device according to claim 32, further including at least one resilient element arranged to provide a bias force toward the non-actuated position.

34. The cooling device according to claim 33, wherein the at least one resilient element is positioned to provide a bias force between said outer jacket and said cover.

35. The cooling device according to claim 1, wherein the device further includes means for adjusting a volume of said chamber independent of movement between the actuated and non-actuated positions.

36. The cooling device according to claim 1, wherein the second opening of the dispensing channel provides an inlet for the refrigerant into the chamber, and wherein the chamber includes at least one vent opening through which the refrigerant can exit said chamber to exit the device, and wherein the at least one vent opening is arranged such that after exiting the container and passing into the chamber the refrigerant in the chamber exits the device through the at least one vent opening without contacting the container prior to exiting the device.

37. The cooling device according to claim 19, wherein the device includes at least one vent through which refrigerant exits the chamber to exit the device without contacting an outer surface of the container prior to exiting the device.

38. The cooling device according to claim 19, further including an actuator arrangement to provide relative movement between the container and said platform, and wherein relative movement between the container and the platform causes actuation of the dispensing device to cause the refrigerant to flow from the container through the platform and into the chamber.

39. The cooling device according to claim 38, wherein the device further includes a jacket at least partially surrounding the container, and wherein the actuator arrangement includes means for allowing relative axial sliding movement between the container and at least one of the cover or the jacket, and wherein said relative axial sliding movement causes movement of the platform relative to the container and said actuation of the dispensing device.

* * * * *